United States Patent [19]
O'Donnell

[11] Patent Number: 5,172,343
[45] Date of Patent: Dec. 15, 1992

[54] ABERRATION CORRECTION USING BEAM DATA FROM A PHASED ARRAY ULTRASONIC SCANNER

[75] Inventor: Matthew O'Donnell, Ann Arbor, Mich.

[73] Assignee: General Electric Company, Schenectady, N.Y.

[21] Appl. No.: 802,804

[22] Filed: Dec. 6, 1991

[51] Int. Cl.⁵ .............................................. G03B 42/06
[52] U.S. Cl. ..................................... 367/7; 367/11; 367/103; 367/105; 364/413.25; 128/661.01; 73/626
[58] Field of Search ..................... 367/7, 11, 103, 105; 73/626; 128/661.01; 364/413.25, 413.13

[56] References Cited
U.S. PATENT DOCUMENTS

| | | | |
|---|---|---|---|
| 4,155,258 | 5/1979 | Engeler et al. | 367/7 |
| 4,155,259 | 5/1979 | Engeler et al. | 367/7 |
| 4,155,260 | 5/1979 | Engeler et al. | 367/7 |
| 4,180,790 | 12/1979 | Thomas | 367/7 |
| 4,217,684 | 8/1980 | Brisken et al. | 310/334 |
| 4,425,525 | 1/1984 | Smith et al. | 310/367 |
| 4,441,503 | 4/1984 | O'Donnell | 128/663.01 |
| 4,470,303 | 9/1984 | O'Donnell | 73/602 |
| 4,470,305 | 9/1984 | O'Donnell | 367/153 |
| 4,662,223 | 5/1987 | Riley et al. | 367/103 |
| 4,669,314 | 6/1987 | Magrane | 73/626 |
| 4,809,184 | 2/1989 | O'Donnell et al. | 128/660.01 |
| 4,835,689 | 5/1989 | O'Donnell | 73/626 |
| 4,989,143 | 1/1991 | O'Donnell et al. | 364/413.25 |

Primary Examiner—Daniel T. Pihulic
Attorney, Agent, or Firm—Marvin Snyder

[57] ABSTRACT

A PASS ultrasonic system performs a scan in which phase errors due to aberrations in the sound media are corrected prior to the acquisition of each beam. Phase errors are measured by cross correlating each of a set of reference beams with the desired beam to produce beam forming errors as a function of beam angle. This function is Fourier transformed to produce phase corrections that are employed by the ultrasonic system to offset the phase errors.

11 Claims, 13 Drawing Sheets

ABERRATION CORRECTION USING BEAM DATA FROM A PHASED ARRAY ULTRASONIC SCANNER

BACKGROUND OF THE INVENTION

This invention relates to coherent imaging systems using vibratory energy, such as ultrasound, and, in particular, to ultrasound imaging systems which employ phased array sector scanning.

There are a number of modes in which vibratory energy, such as ultrasound, can be used to produce images of objects. The ultrasound transmitter may be placed on one side of the object and the sound transmitted through the object to the ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter" or "echo" mode). The present invention relates to a backscatter method for producing ultrasound images.

There are a number of well-known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and either their amplitude or time delay is used to modulate the brightness of pixels on a display. With the B-scan method, enough data are acquired from which an image of the refractors can be reconstructed.

In the so-called C-scan method, the transducer is scanned across a plane above the object and only the echoes reflecting from the focal depth of the transducer are recorded. The sweep of the electron beam of a CRT display is synchronized to the scanning of the transducer so that the x and y coordinates of the transducer correspond to the x and y coordinates of the image.

Ultrasonic transducers for medical applications are constructed from one or more piezoelectric elements sandwiched between a pair of electrodes. Such piezoelectric elements are typically constructed of lead zirconate titanate (PZT), polyvinylidene difluoride (PVDF), or PZT ceramic/polymer composite. The electrodes are connected to a voltage source, and when a voltage is applied, the piezoelectric elements change in size at a frequency corresponding to that of the applied voltage. When a voltage pulse is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere. A number of such ultrasonic transducer constructions are disclosed in U.S. Pat. Nos. 4,217,684; 4,425,525; 4,441,503; 4,470,305 and 4,569,231, all of which are assigned to the instant assignee.

When used for ultrasound imaging, the transducer typically has a number of piezoelectric elements arranged in an array and driven with separate voltages (apodizing). By controlling the time delay (or phase) and amplitude of the applied voltages, the ultrasonic waves produced by the piezoelectric elements (transmission mode) combine to produce a net ultrasonic wave focused at a selected point. By controlling the time delay and amplitude of the applied voltages, this focal point can be moved in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delays (and/or phase shifts) and gains to the signal from each transducer array element.

This form of ultrasonic imaging is referred to as "phased array sector scanning", or "PASS". Such a scan is comprised of a series of measurements in which the steered ultrasonic wave is transmitted, the system switches to receive mode after a short time interval, and the reflected ultrasonic wave is received and stored. Typically, the transmission and reception are steered in the same direction ($\theta$) during each measurement to acquire data from a series of points along a scan line. The receiver is dynamically focused at a succession of ranges (R) along the scan line as the reflected ultrasonic waves are received. The time required to conduct the entire scan is a function of the time required to make each measurement and the number of measurements required to cover the entire region of interest at the desired resolution and signal-to-noise ratio. For example, a total of 128 scan lines may be acquired over a 90 degree sector, with the steering of each scan line being advanced in increments of 0.70°. A number of such ultrasonic imaging systems are disclosed in U.S. Pat. Nos. 4,155,258; 4,155,260; 4,154,113; 4,155,259; 4,180,790; 4,470,303; 4,662,223; 4,669,314 and 4,809,184, all of which are assigned to the instant assignee.

The proper operation of a PASS imaging system presumes that the speed of sound in the media through which the ultrasonic pulses are conveyed is relatively uniform. In medical applications this presumption is usually correct, once the sound propagates through the body wall and enters the internal organs. Quite often, however, irregularities in the body wall itself can produce aberrations. Such aberrations may, for example, slow the sound emanating from certain elements in the array such that they do not have the desired phase when summed with the other signals at the desired focal point. As a result, the delayed ultrasonic signal from these elements may actually subtract from the echo signal produced by a reflector at the focal point and thereby introduce an error, or artifact, in the reconstructed image. In addition, the delay introduced by the aberration is typically not constant as a function of beam steering angle ($\theta$) since the body wall has a finite thickness. Propagation of sound through this inhomogeneous layer of finite thickness at different angles produces different aberrations as a function of the details of the body wall irregularities. Also, in clinical ultrasound applications the body wall moves due to patient breathing and other patient motion, so that aberrations change from scan-to-scan and require recalculation of corrections on a real-time basis.

U.S. Pat. Nos. 4,835,689 and 4,989,143, assigned to the instant assignee, disclose a method and system for correcting the phase of the separate signals produced by the transducer array elements to account for such aberrations. In this prior method, the separate signals produced by each array element are examined and phase corrections for each element are calculated. This approach requires access to the signal produced by each transducer element and requires separate calculation circuitry for each element. In a typical 64 element system, this results in considerable hardware.

SUMMARY OF THE INVENTION

The present invention relates to a method and apparatus for correcting phase errors in a PASS imaging system caused by aberrations in the sound media, and particularly, to the calculation of correction phases for each transducer element using acquired beam data. More specifically, the present invention includes a multi-element ultrasonic transducer; a transmitter which applies pulses to the separate transducer elements delayed by amounts necessary to steer an ultrasonic beam in a desired direction ($\theta$); a receiver responsive to each transducer element and which provides a separate delay to the echo signal produced by each element to form a plurality of receive beams, one of which is steered in the desired direction ($\theta$); and an aberration correction processor responsive to the receiver and operable to calculate the cross correlation of the simultaneously formed receive beams in order to measure the complex error ($A\theta$, $\Delta\phi\theta$) between an echo signal from the steering direction $\theta$ and the echo signals from other reference steering angles. The aberration correction processor is also operable to Fourier transform the set of measured errors ($A\theta$, $\Delta\phi\theta$) to produce a set of correction phase $\Delta\phi_k$ changes are applied to correct the timing of the pulses applied to the respective transducer elements by the transmitter and which are applied to correct the delays imposed by the receiver on the echo signals produced by the respective transducer elements. As a result, when a subsequent beam is transmitted and received along the steering direction $\theta$, artifacts caused by aberrations in the beam path are reduced.

A general object of the invention is to correct for aberrations in the sound transmission media by using the receive beam data. Two simultaneously-produced receive beams should have the same phase at equal ranges if the media through which they travel is acoustically homogeneous. To the extent they do not, a phase difference can be measured by cross correlating the two beams. By producing a set of such simultaneous beams and measuring the difference of each with respect to the receive beam at the desired steering angle ($\theta$), a set of phase correction values can be produced for the receiver and the transmitter. These correction values are used in the subsequent acquisition of a complete transmit/receive beam at the desired steering angle ($\theta$). The process is repeated for other steering angles until the sector scan is completed.

Another object of the invention is to reduce complexity of the circuitry required to correct for aberrations in the sound transmission media. The receive beam data are processed by a single correlation and Fourier transform processor to produce the separate phase correction values $\Delta\phi_k$. This is in contrast to prior systems which employ separate circuitry for each receiver channel.

Yet another object of the invention is to acquire measurements from which phase corrections can be made even when there is movement of the reflectors in the subject under examination. This is accomplished by producing simultaneous receive beams which "see" the same reflectors and which, therefore, facilitate accurate measurement of the phase difference caused by aberrations in the sound transmission media.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIGS. 2A and 2B are graphical illustrations of the signal in any of the channels of transmitter 50 of FIG. 2;

DESCRIPTION OF THE PREFERRED EMBODIMENT

Figure 1:
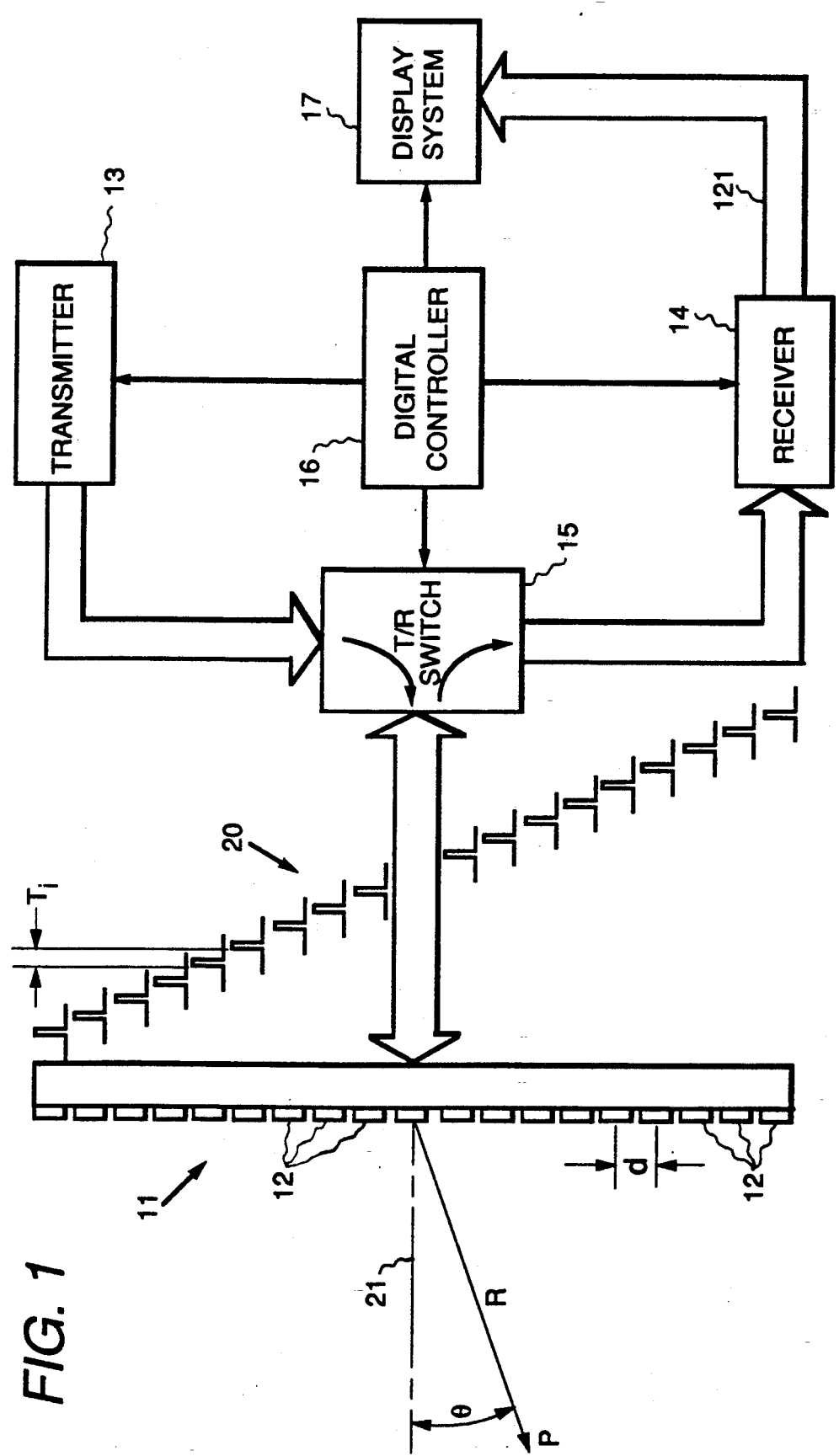
FIG. 1 is a block diagram of an ultrasonic imaging system which employs the present invention.

Referring particularly to FIG. 1, a vibratory energy imaging system includes a transducer array 11 comprised of a plurality of separately driven elements 12 which each produce a burst of vibratory energy, such as ultrasonic energy, when energized by a pulse produced by a transmitter 13. The vibratory energy reflected back to transducer array 11 from the subject under study is converted to an electrical signal by each transducer element 12 and applied separately to a receiver 14 through a set of switches 15. Transmitter 13, receiver 14 and switches 15 are operated under control of a digital controller 16 responsive to commands by a human operator. A complete scan is performed by acquiring a series of echoes in which switches 15 are set to their transmit position, transmitter 13 is gated on momentarily to energize each transducer element 12, switches 15 are then set to their receive position, and the subsequent echo signals produced by each transducer element 12 are applied to receiver 14. The separate echo signals from each transducer element 12 are combined in receiver 14 to produce a single echo signal which is employed to produce a line in an image on a display system 17.

Transmitter 13 drives transducer array 11 such that the vibratory energy produced, e.g., ultrasonic energy, is directed, or steered, in a beam. A B-scan can therefore be performed by moving this beam through a set of angles from point-to-point rather than physically moving transducer array 11. To accomplish this, transmitter 13 imparts a time delay $(T_i)$ to the respective pulses 20 that are applied to successive transducer elements 12. If the time delay is zero $(T_i=0)$, all the transducer elements 12 are energized simultaneously and the resulting ultrasonic beam is directed along an axis 21 normal to the transducer face and originating from the center of transducer array 11. As the time delay $(T_i)$ is increased, as illustrated in FIG. 1, the ultrasonic beam is directed downward from central axis 21 by an angle $\theta$. The relationship between the time delay increment $T_i$ added successively to each $i_{th}$ signal from one end of the transducer array $(i=1)$ to the other end $(i=N)$ is given by the following relationship:

$$T_i = -(i-(n-1)/2)d \sin \theta/c + (i-(n-1)/2)^2 d^2 \cos^2\theta/2R_Tc + T_O \quad (1)$$

where d = equal spacing between centers of adjacent transducer elements 12,
c = velocity of sound in the object under study,
$R_r$ = range at which transmit beam is to be focused, and
$T_O$ = delay offset which insures that all calculated values $(T_i)$ are positive values.

The first term in this expression steers the beam in the desired angle $\theta$, and the second is employed when the transmitted beam is to be focused at a fixed range. A sector scan is performed by progressively changing time delays $t_i$ in successive excitations. The angle $\theta$ is thus changed in increments to steer the transmitted beam in a succession of directions. When the direction of the beam is above central axis 21, the timing of pulses 20 is reversed, but the formula of equation (1) still applies.

Referring still to FIG. 1, the echo signals produced by each burst of ultrasonic energy emanate from reflecting objects located at successive positions along the ultrasonic beam. These are sensed separately by each segment 12 of transducer array 11 and a sample of the magnitude of the echo signal at a particular point in time represents the amount of reflection occurring at a specific range (R). Due to differences in the propagation paths between a focal point P and each transducer element 12, however, these echo signals will not occur simultaneously and their amplitudes will not be equal. The function of receiver 14 is to amplify and demodulate these separate echo signals, impart the proper time delay to each and sum them together to provide a single echo signal which accurately indicates the total ultrasonic energy reflected from each focal point P located at range R along the ultrasonic beam oriented at the angle $\theta$.

To simultaneously sum the electrical signals produced by the echoes from each transducer element 12, time delays are introduced into each separate transducer element channel of receiver 14. In the case of linear array 11, the delay introduced in each channel may be divided into two components; one component is referred to as a beam steering time delay, and the other component is referred to as a beam focusing time delay. The beam steering and beam focusing time delays for reception are precisely the same delays $(T_i)$ as the transmission delays described above. However, the focusing time delay component introduced into each receiver channel is continuously changing during reception of the echo to provide dynamic focusing of the received beam at the range R from which the echo signal emanates. This dynamic focusing delay component is as follows:

$$T_k = (k-(n-1)/2)^2 d^2 \cos^2 \theta/2Rc \quad (2)$$

where R = range of the focal point P from the center of array 11,
C = velocity of sound in the object under study, and
$T_k$ = desired time delay associated with the echo signal from the kth element to coherently sum it with the other echo signals.

Under direction of digital controller 16, receiver 14 provides delays during the scan such that steering of receiver 14 tracks with the direction $(\theta)$ of the beam steered by transmitter 13 and it samples the echo signals at a succession of ranges (R) and provides the proper delays to dynamically focus at points P along the beam. Thus, each emission of an ultrasonic pulse results in reception of a series of echo signal samples which represent the amount of reflected sound from a corresponding series of points P located along the ultrasonic beam. Receiver 14 is able to change its delays for each echo signal sample to dynamically focus on the reflectors which produce the signal sample. The stream of focused and steered echo signal samples which are produced by the receiver is referred to in the art as the "received beam".

Display system 17 receives the series of data samples produced by receiver 14 and converts the data to a form producing the desired image. For example, if an A-scan is desired, the magnitude of the series of data points is merely graphed as a function of time. If a B-scan is desired, each data point in the series is used to control brightness of a pixel in the image, and a scan comprised of a series of measurements at successive steering angles ($\theta$) is performed to provide the data necessary for display.

Figure 7:
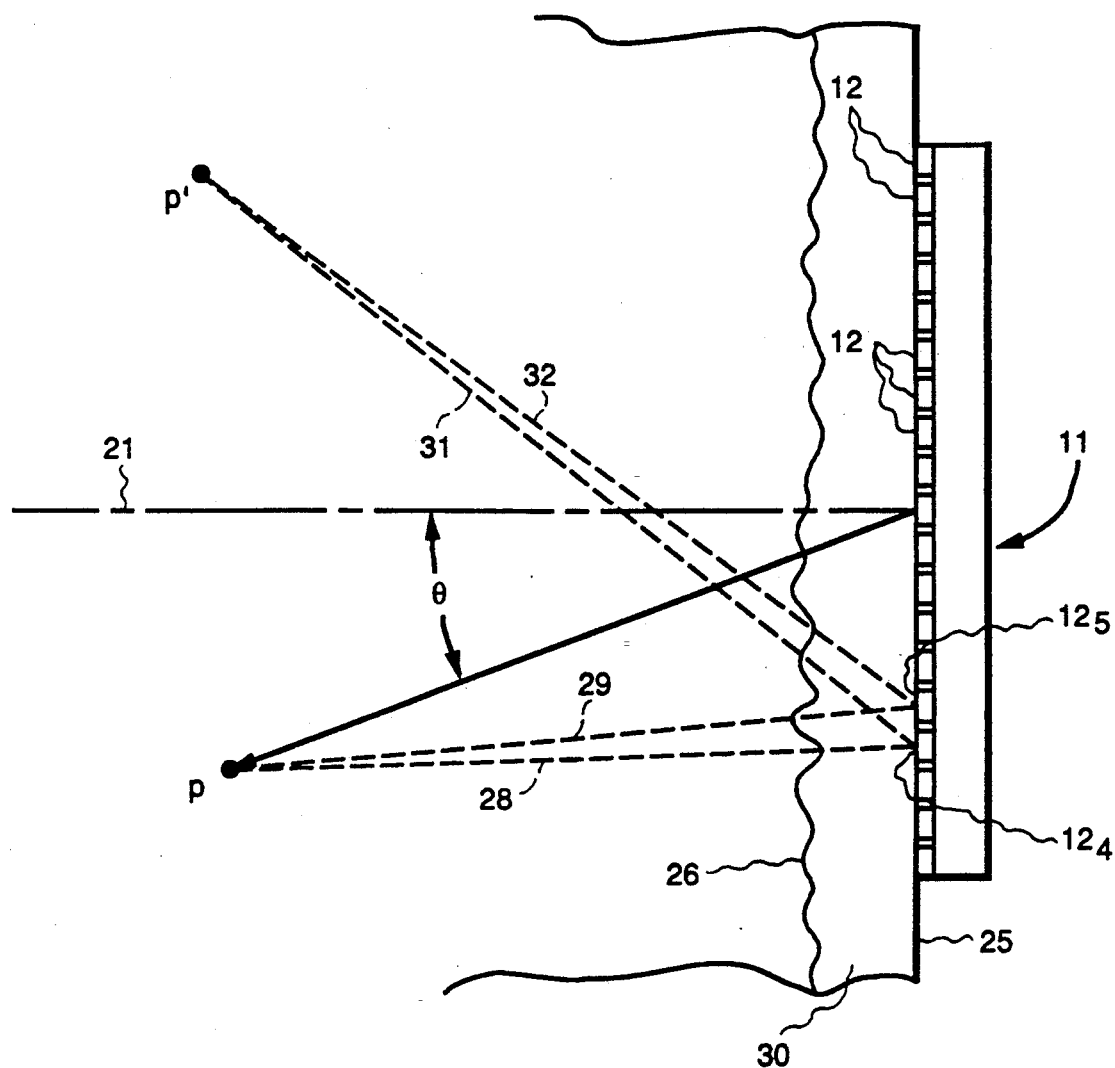
FIG. 7 is a schematic representation of the ultrasonic transducer used in the system of FIG. 1 which illustrates the effect of aberrations in the sound transmission media.

It can be appreciated that the time delays produced in accordance with equation (1) to provide the desired steering and focusing during both the transmit mode and receive mode presume that the sound travels at a uniform velocity c throughout the sound propagating media. In clinical applications this is usually not the case. Instead, as illustrated in FIG. 7, ultrasonic transducer 11 is typically placed on the patient's skin 25 and sound emanating therefrom passes through one or more layers of tissue which have different sound propagating properties. A boundary 26 between such layers has an irregular shape. As a result, for example, when beam samples are being acquired from point P at steering angle $\theta$, sound conveyed between point P and two separate array elements $12_4$ and $12_5$ is propagated quite differently due to the irregularity of boundary 26. This is illustrated by the respective dashed lines 28 and 29 which reveal that the ultrasound path length in tissue layer 30 is longer for transducer element $12_5$ than for transducer element $12_4$. This difference in path length in tissue layer 30 to the two transducer elements causes the phase aberration. The same tissue layer may or may not affect the phase of sound associated with others of transducer elements 12, and the same tissue layer may or may not affect the phase of the sound associated with the same elements $12_4$ and $12_5$ at different steering angles $\theta$. This is illustrated by sound paths 31 and 32 to a point P', which paths have very similar lengths in tissue layer 30.

The corrections for phase errors caused by aberrations in the sound propagating media are different for each transducer element 12 and for each steering angle $\theta$ acquired during the scan. According to the present invention, the phase corrections $\Delta\phi_k$ required by the signals associated with each transducer element 12 in order to offset the errors caused by aberrations in the sound media are calculated, and those corrections are applied to the time delays $T_i$ produced by transmitter 13 and imposed by receiver 14, shown in FIG. 1.

Figure 2:
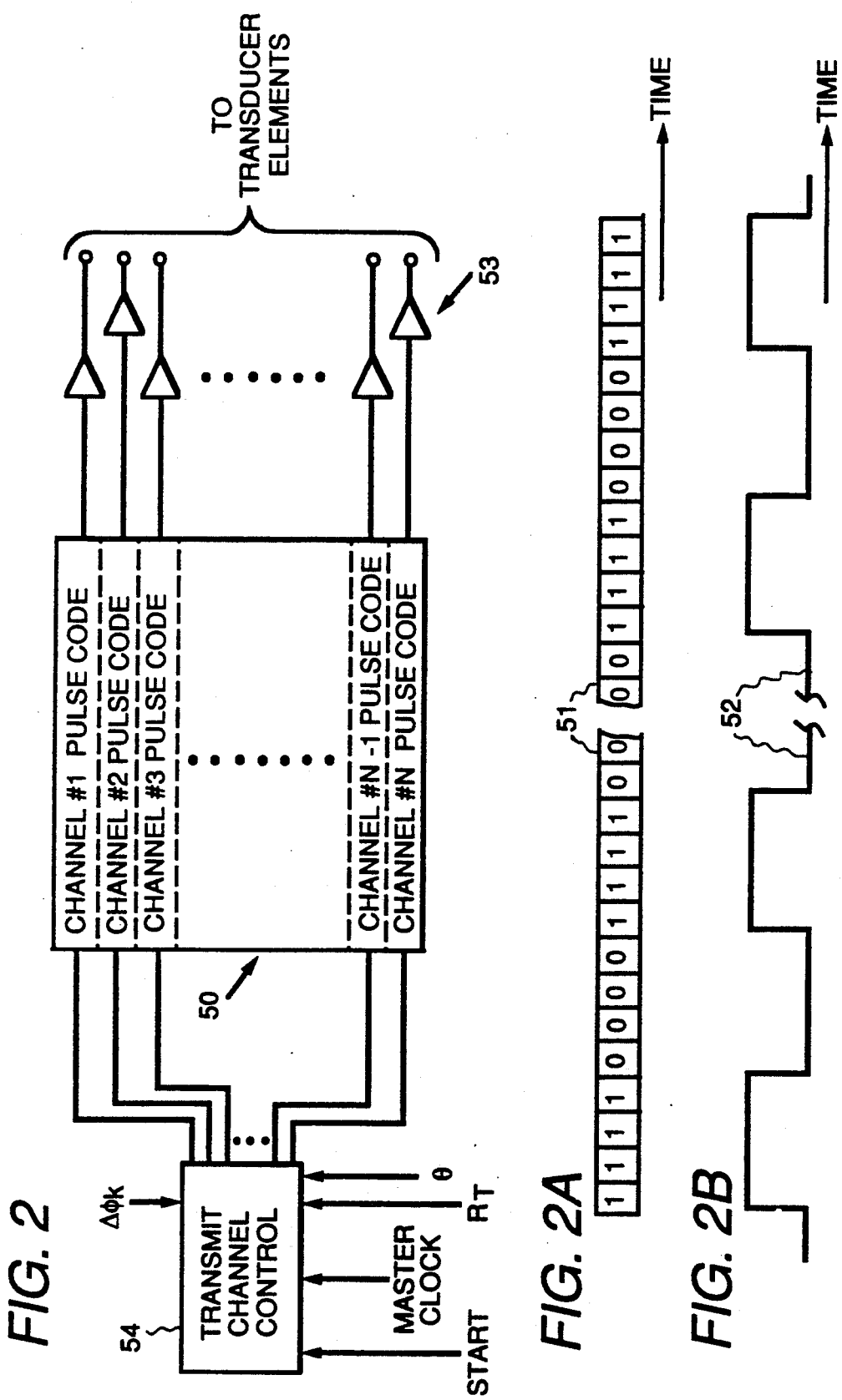
FIG. 2 is a block diagram of a transmitter which forms part of the system of FIG. 1.

Referring to FIG. 2 in conjunction with FIG. 1, transmitter 13 includes a set of channel pulse code memories indicated collectively as memories 50. In the preferred embodiment, there are 64 separate transducer elements 12, and therefore, there are 64 separate channel pulse code memories 50. Each pulse code memory 50 is typically a 1-bit by 512-bit memory which stores a bit pattern 51 that determines the frequency of ultrasonic pulse 52 to be produced. In the preferred embodiment, this bit pattern is read out of each pulse code memory 50 by a 40 MHz master clock and applied to a driver 53 which amplifies the signal to a power level suitable for driving transducer 11. Transducer elements 12 to which these ultrasonic pulses 52 are applied respond by producing ultrasonic energy. If all 512 bits are used, then a pulse of bandwidth as narrow as 40 kHz centered on the carrier frequency will be emitted.

As indicated above, to steer the transmitted beam of the ultrasonic energy in the desired direction ($\theta$), pulses 52 for each of the N channels, such as shown in FIG. 2B, must be delayed by the proper amount. These delays are provided by a transmit control 54 which receives four control signals (START, MASTER CLOCK, $R_T$ and $\theta$) from digital controller 16 (FIG. 1). Using the input control signal $\theta$, the fixed transmit focus $R_T$, and the above equation (1), transmit control 54 calculates the delay increment $T_i$ required between successive transmit channels. When the START control signal is received, transmit control 54 gates one of four possible phases of the 40 MHz MASTER CLOCK signal through to the first transmit channel 50. At each successive delay time interval ($T_i$) thereafter, one of the phases of the 40 MHz MASTER CLOCK signal is gated through to the next channel pulse code memory 50 until all N=64 channels are producing their ultrasonic pulses 52. Each transmit channel 50 is reset after its entire bit pattern 51, such as shown in FIG. 2A, has been transmitted and transmitter 13 then waits for the next $\theta$ and next START control signals from digital controller 16. As indicated above, in the preferred embodiment of the invention, a complete B-scan is comprised of 128 ultrasonic pulses steered in $\Delta\theta$ increments of 0.70 degrees through a 90 degree sector centered about the central axis 21 (FIG. 1) of the transducer 11.

For a detailed description of transmitter 13, reference is made to commonly assigned U.S. Pat. No. 5,014,712, issued Jan. 28, 1991 and entitled "Coded Excitation for Transmission Dynamic Focusing of Vibratory Energy Beam", incorporated herein by reference.

Figure 3:
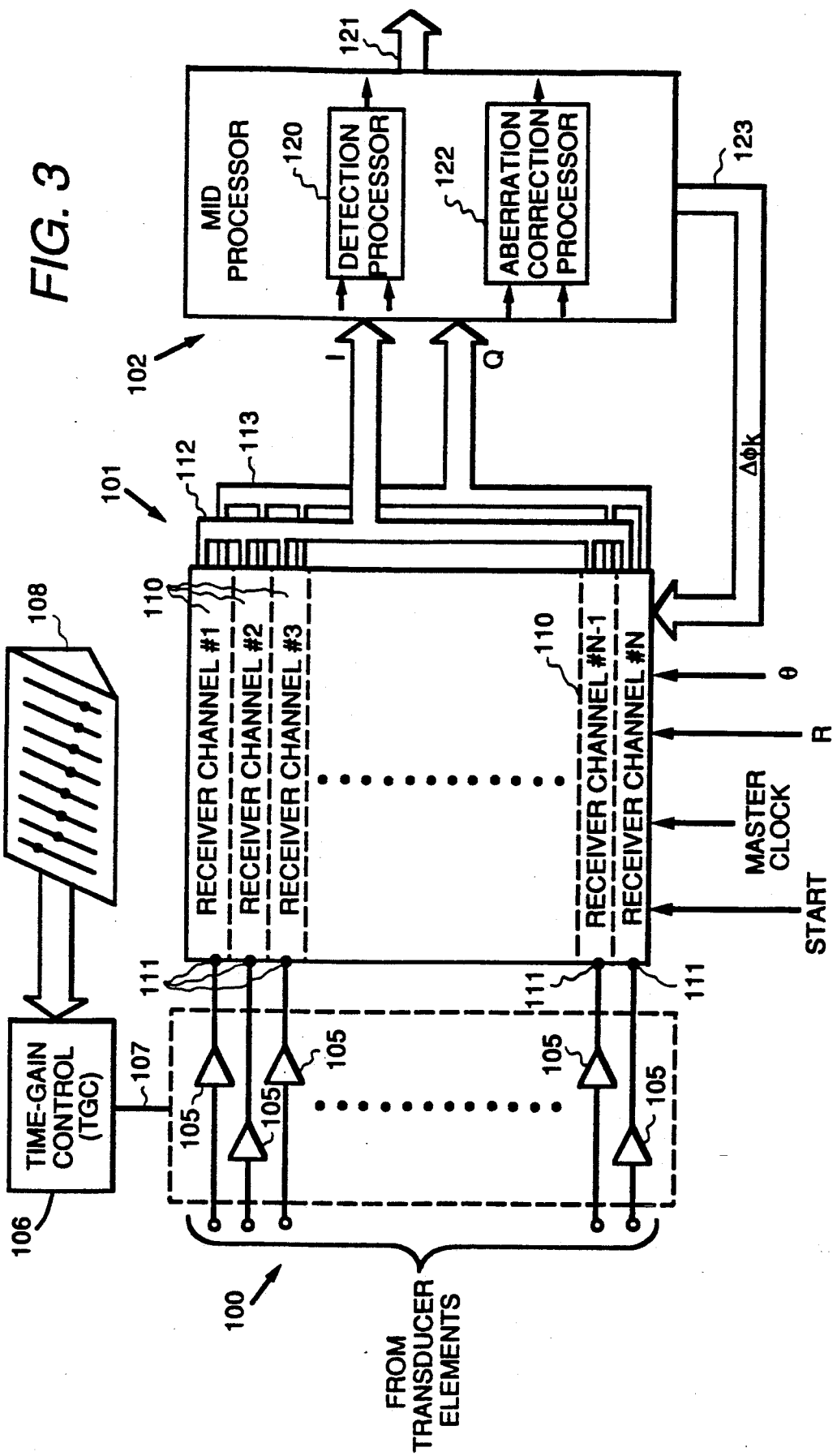
FIG. 3 is a block diagram of a receiver which forms part of the system of FIG. 1.

Referring particularly to FIG. 3 in conjunction with FIG. 1, receiver 14 is comprised of three sections: a time-gain control section 100, a receive beam forming section 101, and a mid processor 102. Time-gain control section 100 includes an amplifier 105 for each of the N=64 receiver channels and a time gain control circuit 106. The input of each amplifier 105 is connected to a respective one of transducer elements 12 to receive and amplify the echo signal which it receives. The amount of amplification provided by amplifiers 105 is controlled through a control line 107 that is driven by time-gain control circuit 106. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets eight (typically) TGC linear potentiometers 108 to values which provide a relatively uniform brightness over the entire range of the sector scan. The time interval over which the echo signal is acquired determines the range from which it emanates, and this time interval is divided into eight segments by TGC control circuit 106. The settings of the eight potentiometers are employed to set the gains of amplifiers 105 during each of the eight respective time intervals so that the echo signal is amplified in ever increasing amounts over the echo signal acquisition time interval.

The receive beam forming section 101 of receiver 14 includes N=64 separate receiver channels 110. As will be explained in more detail below, each receiver channel 110 receives the analog echo signal from one of TGC amplifiers 105 at an input 111, and it produces a stream of digitized output values on an I bus 112 and a Q bus 113. Each of these I and Q values represents a sample of the echo signal envelope at a specific range (R). These samples have been delayed in the manner described above such that when they are summed at summing points 114 and 115 with the I and Q samples from each of the other receiver channels 110, they indicate the magnitude and phase of the echo signal reflected from a point P located at range R on the steered beam ($\theta$). In the preferred embodiment, each echo signal is sampled at equal intervals of about 150 micrometers over the entire range of the scan line (typically 40 to 200 millimeters).

For a more detailed description of receiver 14, reference is made to U.S. Pat. No. 4,983,970 which issued on Jan. 8, 1991 and is entitled "Method and Apparatus for Digital Phase Array Imaging", and which is incorporated herein by reference.

Referring still to FIG. 3, mid processor section 102 receives the receive beam samples from summing points 114 and 115. The I and Q values of each beam sample are 16-bit digital numbers representing the in-phase and quadrature components of the magnitude of reflected sound from a point (R,θ). Mid processor 102 can perform a variety of calculations on these beam samples, where choice is determined by the type of image to be reconstructed. For example, if a conventional magnitude image is to be produced, a detection processor 120 is implemented in which a digital magnitude M is calculated from each receive beam sample and produced at output at 121 according to $$M = \sqrt{I^2 + Q^2}.$$

The present invention is implemented in large part by an aberration correction processor 122 contained in mid processor 102 and described in detail below. Aberration correction processor 122 receives the I and Q components of two simultaneously produced beam samples from beam forming section 101 and calculates phase correction values $\Delta\phi_k$ which are produced at mid processor output 123. These phase correction values $\Delta\phi_k$ are applied to transmitter 13 of FIG. 1 as described above, and they are applied to the separate channels 110 of the receiver beam forming section, as described in detail below. During a scan, at each steering angle θ data are first acquired and used by aberration correction processor 122 to produce the phase correction values $\Delta\phi_k$. On the next acquisition along this beam, either in the next image frame or on a subsequent firing in the same image frame, image data are acquired with the phase corrections in place. The image data are used by detection processor 120 to produce the data for display system 17 of FIG. 1.

Figure 4:
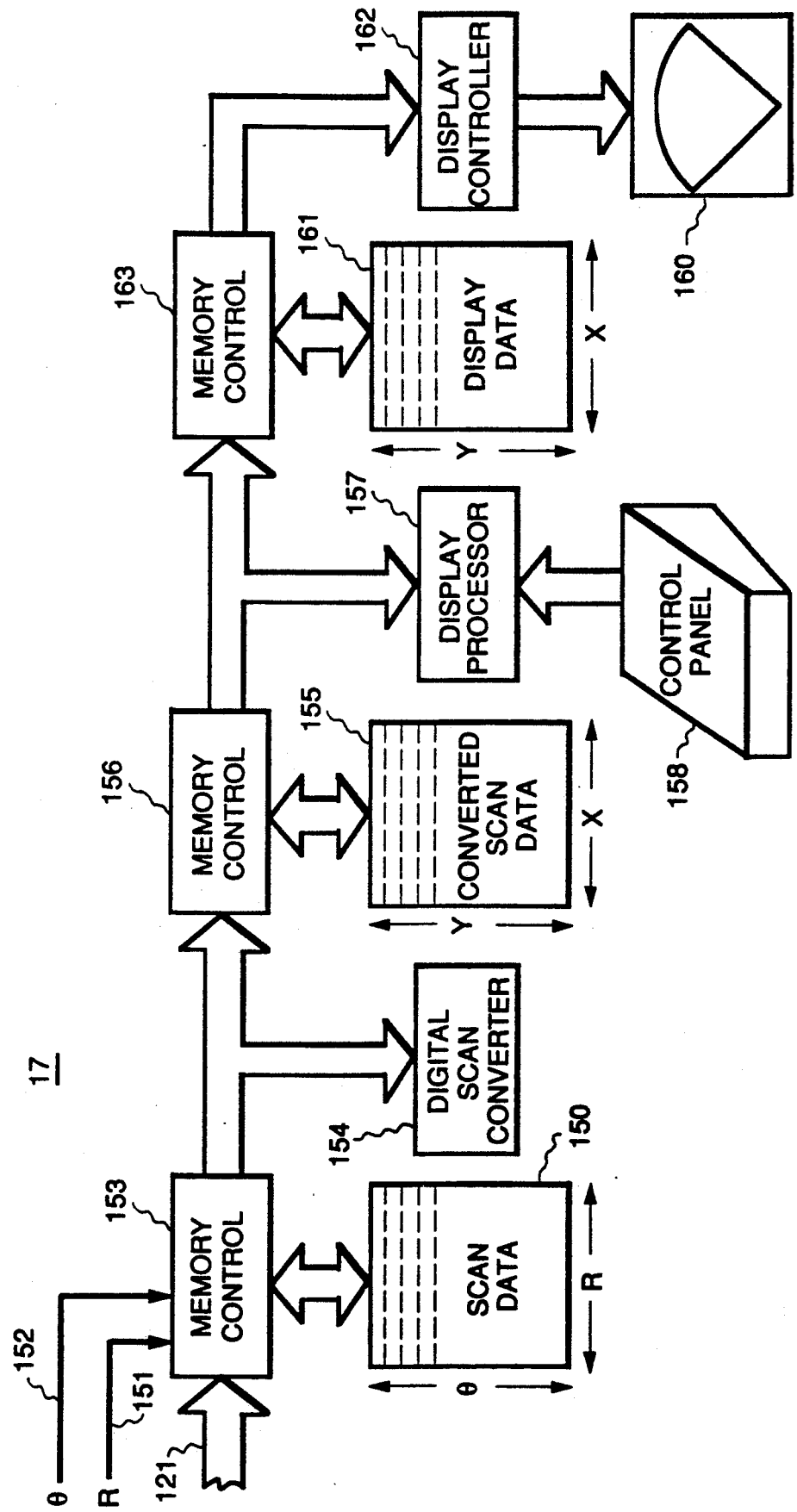
FIG. 4 is a block diagram of a display system which forms part of the system of FIG. 1.

Referring particularly to FIGS. 1 and 4, receiver 14 generates a stream of 8-bit digital numbers at its output 121, which is applied to the input of display system 17. This "scan data" is stored in a memory 150 as an array, with the rows of scan data array 150 corresponding with the respective beam angles (θ) that are acquired, and the columns of scan data array 150 corresponding with the respective ranges (R) at which samples are acquired along each beam. The R and θ control signals 151 and 152 from receiver 14 indicate where each input value is to be stored in array 150, and a memory control circuit 153 writes that value to the proper memory location in array 150. The scan can be continuously repeated and the flow of values from receiver 14 will continuously update scan data array 150.

Referring still to FIG. 4, the scan data in array 150 are read by a digital scan converter 154 and converted to a form producing the desired image. If a conventional B-scan image is being produced, for example, the magnitude values M(R,θ) stored in scan data array 150 are converted to magnitude values M(x,y) which indicate magnitudes at pixel locations (x,y) in the image. Such a polar coordinate to Cartesian coordinate conversion of the ultrasonic image data is described, for example, in an article by Steven C. Leavitt et al. in *Hewlett-Packard Journal*, Oct., 1983, pp. 30–33, entitled "A Scan Conversion Algorithm for Displaying Ultrasound Images".

Regardless of the particular conversion made by digital scan converter 154, the resulting image data are written to a memory 155 which stores a two-dimensional array of converted scan data. A memory control 156 provides dual-port access to memory 155 such that the digital scan converter 154 can continuously update the values therein with fresh data while a display processor 157 reads the updated data. Display processor 157 is responsive to operator commands received from a control panel 158 to perform conventional image processing functions on the converted scan data in memory 155. For example, the range of brightness levels indicated by the converted scan data in memory 155 may far exceed the brightness range of display device 160. Indeed, the brightness resolution of the converted scan data in memory 155 may far exceed the brightness resolution of the human eye, and manually operable controls are typically provided which enable the operator to select a window of brightness values over which maximum image contrast is to be achieved. The display processor reads the converted scan data from memory 155, provides the desired image enhancement, and writes the enhanced brightness values to a display memory 161.

Display memory 161 is shared with a display controller circuit 162 through a memory control circuit 163, and the brightness values therein are mapped to control brightness of the corresponding pixels in display 160. Display controller 162 is a commercially available integrated circuit designed to operate the particular type of display 160 used. For example, display 160 may be a CRT (cathode ray tube), in which case display controller 162 is a CRT controller chip which provides the required sync pulses for the horizontal and vertical sweep circuits and maps the display data to the CRT at the appropriate time during the sweep.

It should be apparent to those skilled in the art that display system 17 may take one of many forms depending on the capability and flexibility of the particular ultrasound system. In the preferred embodiment described above, programmed microprocessors are employed to implement the digital scan converter and display processor functions, and the resulting display system is, therefore, very flexible and powerful.

Figure 5:
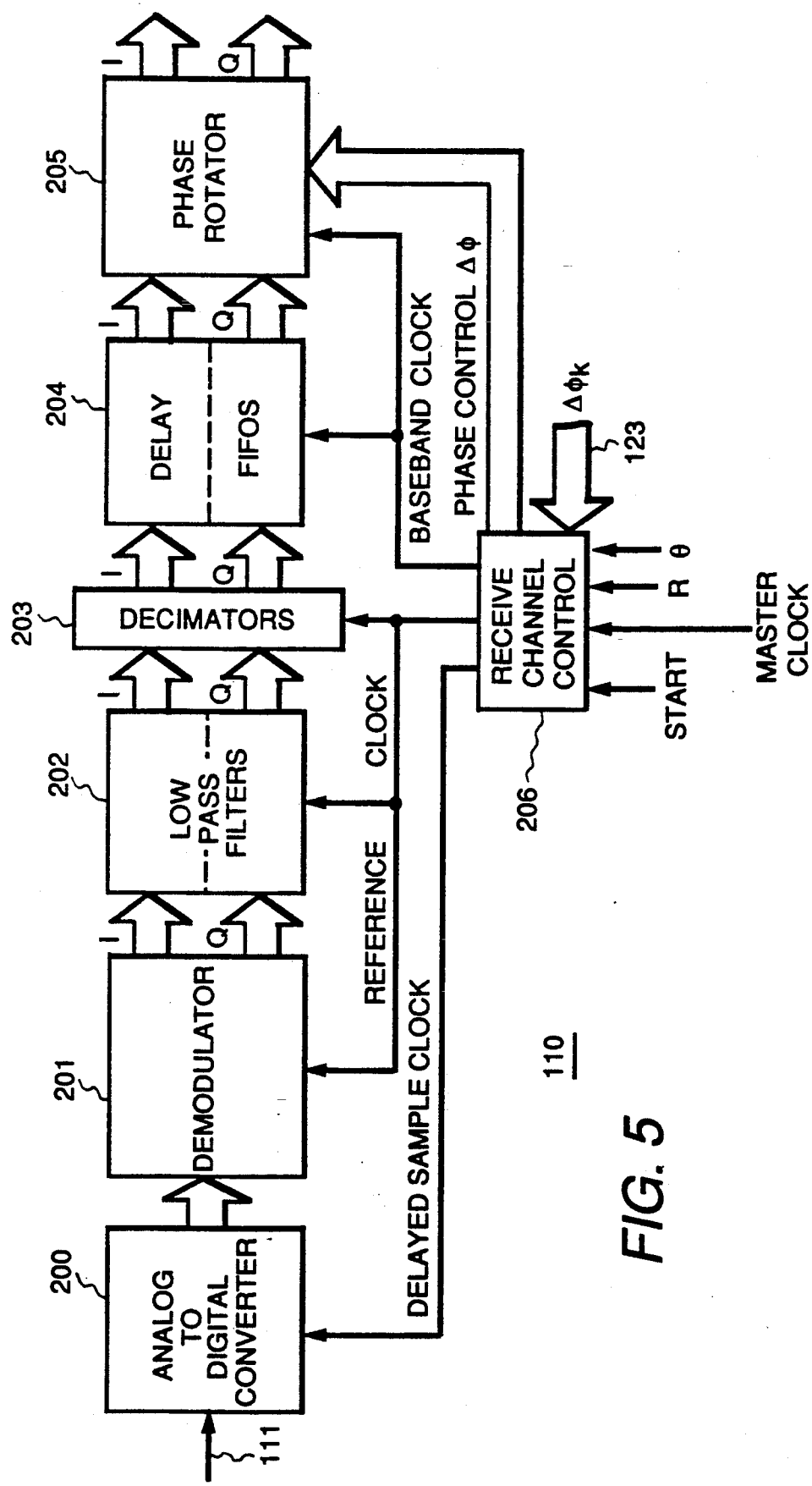
FIG. 5 is a block diagram of a receiver channel which forms part of the receiver of FIG. 3.

As indicated above with reference to FIG. 3, beam forming section 101 of receiver 14 is comprised of a set of receiver channels 110—one for each element 12 of transducer 11 (FIG. 1). Referring particularly to FIG. 5, each receiver channel is responsive to a START command, a 40 MHz master clock, a range signal (R) and a beam angle signal (θ) from digital controller 16 (FIG. 1) to perform the digital beam forming functions. These include: sampling the analog input signal in an analog-to-digital converter 200, demodulating the sampled signal in a demodulator 201; filtering out the high frequency sum signals produced by demodulator 201 with low pass filters 202; reducing the data rate in decimators 203; and time delaying and phase adjusting the resulting digital data stream in delay FIFOs (i.e., first-in/first-out memories) 204 and phase rotator 205. All of these elements are controlled by a receive channel control 206 which produces the required clock and control signals in response to commands from digital controller 16 (FIG. 1). In addition, an aberration correction phase $\Delta\phi_k$ is also provided to receive channel control 206 and added to the normal delay $T_k$ imposed on the echo signal. In the preferred embodiment all of these elements are contained on a single integrated circuit.

Figure 14E:
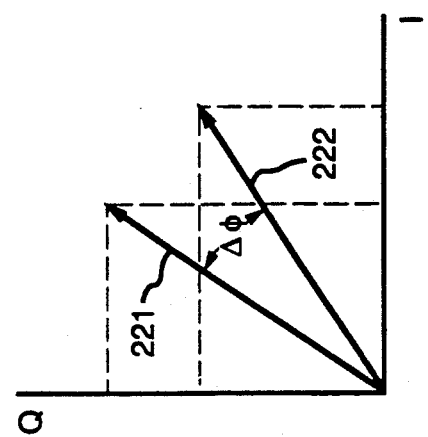
FIGS. 14A-14E are graphical illustrations of the signal at various points in the receiver channel of FIG. 5.
Figure 14B:
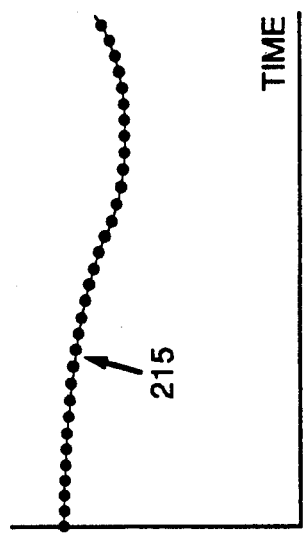
Figure 14D:
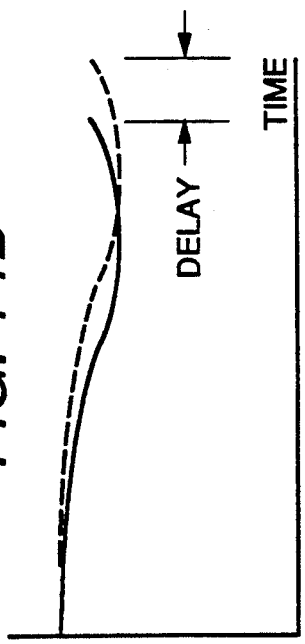
Figure 14A:
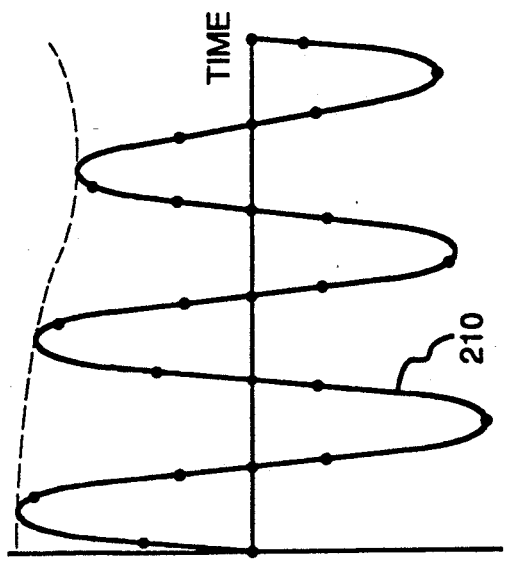

Referring still to FIG. 5, analog-to-digital converter 200 samples the analog input signal, indicated graphically by waveform 210 in FIG. 14A, at regular intervals determined by the leading edge of a delayed sample clock signal from receive channel control 206. In the preferred embodiment, the sample clock signal is a 40 MHz clock signal to enable use of ultrasonic frequencies up to 20 MHz without violating the Nyquist sampling criteria. When a 5 MHz ultrasonic carrier frequency is employed, for example, it is sampled eight times per carrier cycle and a 10-bit digital sample is produced at the output of the analog-to-digital converter at a 40 MHz rate. These samples are supplied to demodulator 201 which mixes each sample with both a reference in-phase with the transmitted ultrasonic carrier, and with a reference in quadrature with the transmitted ultrasonic carrier. The demodulator reference signals are produced from stored SINE and COSINE tables that are read out of their respective ROM memories by a 40 MHz reference clock signal from receive channel control 206. The SINE value is digitally multiplied by the sampled input signal to produce a demodulated, in-phase value (I) supplied to low pass filter 202, and the COSINE value is digitally multiplied by the same sampled input signal to produce a demodulated, quadrature phase value Q output signal to a separate low pass filter 202. Low pass filters 202 are finite impulse response filters tuned to pass the difference frequencies supplied by demodulator 201, but block the higher, sum frequencies. As shown by waveform 215 in the graph of FIG. 14B, the output signal of each low pass filter is, therefore, a 40 MHz stream of digital values which indicate the magnitude of the I or Q component of the echo signal envelope.

For a detailed description of an analog-to-digital converter, demodulator, and a low pass filter circuit, reference is made to commonly assigned U.S. Pat. No. 4,839,652 which issued Jun. 13, 1989 and is entitled "Method and Apparatus for High Speed Digital Phased Array Coherent Imaging System".

Figure 14C:
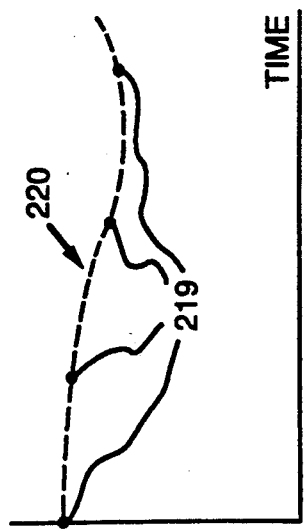

Referring still to FIG. 5, the rate at which the demodulated I and Q components of the echo signal are sampled is reduced by decimators 203. The 12-bit digital samples are supplied to the decimators at a 40 MHz rate which is unnecessarily high from an accuracy standpoint, and which is a difficult data rate to maintain throughout the system. Accordingly, decimators 203 select every eighth digital sample to reduce the data rate down to a 5 MHz rate. This corresponds to the frequency of a baseband clock signal produced by receive channel control 206 and employed to operate the remaining elements in the receiver channel. The I and Q output signals of decimators 203 are thus digitized samples 219 of the echo signal envelope indicated by dashed line 220 in the graph of FIG. 14C. The decimation ratio and the baseband clock frequency can be changed to values other than 8:1 and 5 MHz.

The echo signal envelope represented by the demodulated and decimated digital samples is then delayed by delay FIFOs 204 and phase rotator 205 to provide the desired beam steering and beam focusing. These delays are in addition to the coarse delays provided by the timing of the delayed sample clock signal applied to analog-to-digital converter 200 as described above. That is, the total delay provided by receiver channel 110 is the sum of the delays provided by the delayed sample clock signal supplied to analog-to-digital converter 200, delay FIFOs 204 and phase rotator 205. This total delay is equal to the calculated value $T_i$ in accordance with equation (1), plus the delay represented by the aberration phase correction $\Delta\phi_k$. The delay FIFOs 204 are memory devices into which the successive digital sample values are written as they are produced by the decimators 203 at a rate of 5 MHz. These stored values are written into successive memory addresses and then read from the memory device and supplied to phase rotator 205. The amount of delay, illustrated graphically in FIG. 14D, is determined by the difference between the memory location from which the digital sample is currently being supplied and the memory location into which the currently received digital sample is being stored. The 5 MHz baseband clock signal establishes 200 nanosecond intervals between stored digital samples and FIFOs 204 can, therefore, provide a time delay measured in 200 nanosecond increments up to their maximum of 25.6 microseconds.

Phase rotator 205 enables the digitized representation of the echo signal to be delayed by amounts less than the 200 nanosecond resolution of delay FIFOs 204. The I and Q digital samples supplied to phase rotator 205 may be represented, as shown in FIG. 14E, by a phasor 221 and the rotated I and Q digital samples produced by phase rotator 205 may be represented by a phasor 222. The magnitudes of the phasors (i.e. the vector sum of the I and Q components of each) are not changed, but the I and Q values are changed with respect to one another such that the output phasor 222 is rotated by an amount $\Delta\phi$ from the input phasor 221. The phase can be either advanced $(+\Delta\phi)$ or delayed $(-\Delta\phi)$ in response to a phase control signal received on a bus from receive channel control 206. For a detailed description of phase rotator 205, reference is made to commonly assigned U.S. Pat. No. 4,896,287 which issued on Jan. 23, 1990, entitled "Cordic Complex Multiplier", and incorporated herein by reference.

Figure 6:
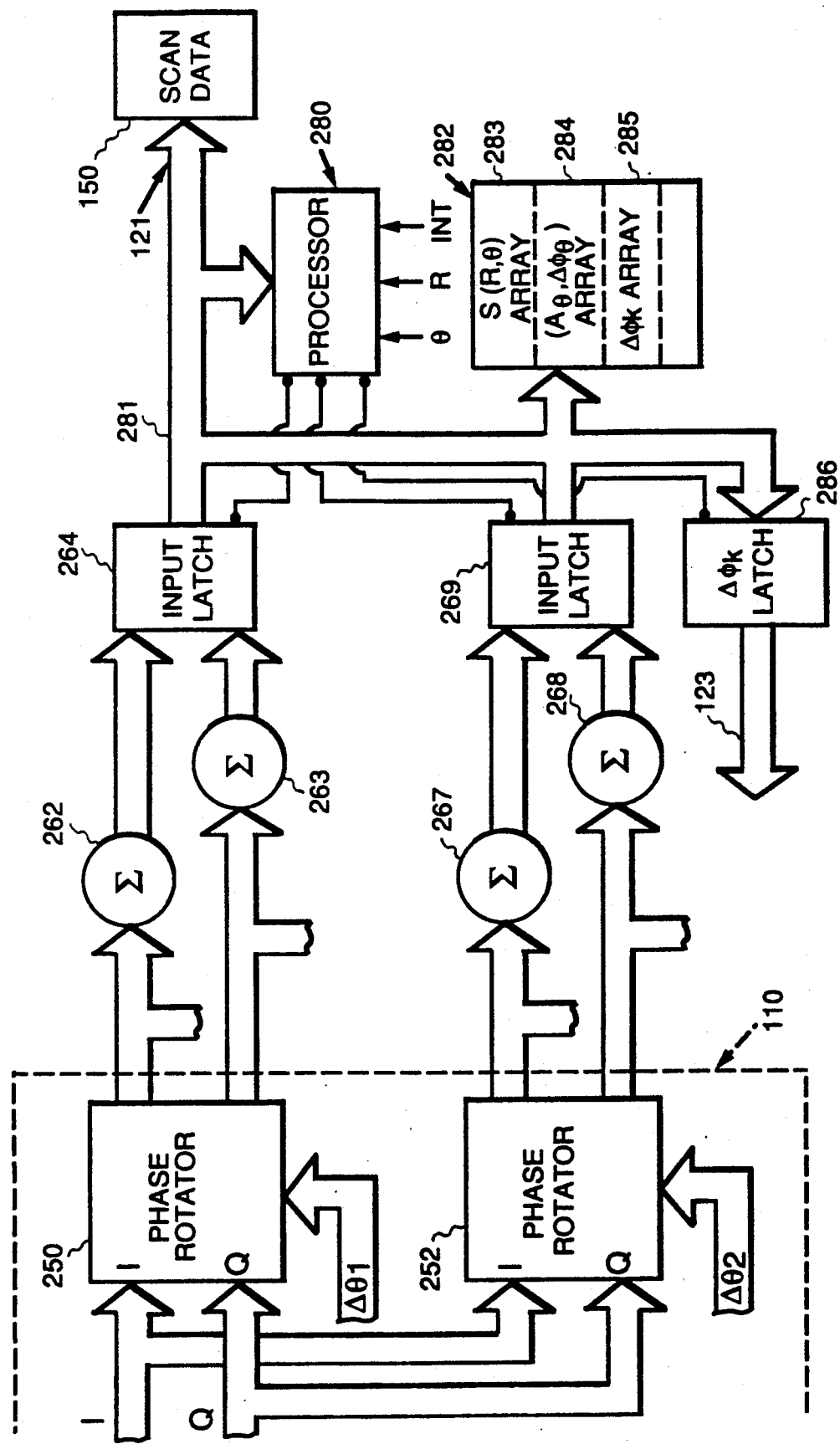
FIG. 6 is an electrical block diagram of the mid-processor which forms part of the receiver of FIG. 3.
Figure 8:
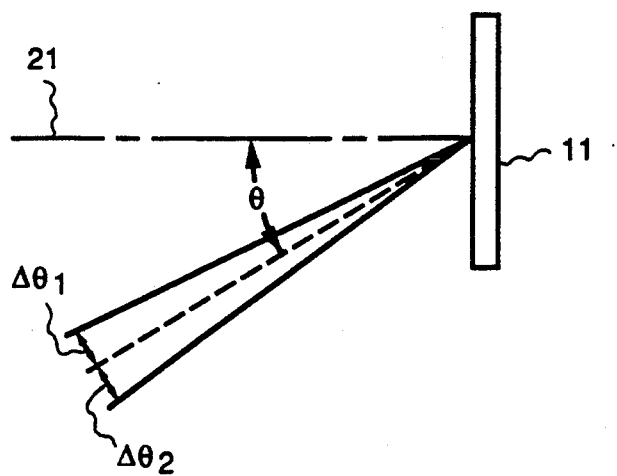
FIG. 8 is a schematic representation of the ultrasonic transducer which illustrates the production of two simultaneous receive beams.

Referring to FIG. 6, the I and Q output signals of each channel receiver 110 are supplied to first and second phase rotators 250 and 252. Phase rotators 250 and 252 may be included as part of each receiver channel 110. Phase rotators 250 and 252 form two receive beams as described in U.S. Pat. No. 4,886,069 which issued on Dec. 12, 1989 and is hereby incorporated by reference, and is entitled "Method Of, And Apparatus For, Obtaining A Plurality Of Different Return Energy Imaging Beams Responsive To A Single Excitation Event." Each of phase rotators 250 and 252 is identical to phase rotator 205 (FIG. 5) described above, and receives phase shift commands $\Delta\theta_1$ and $\Delta\theta_2$ respectively from the digital controller 16 (FIG. 1). The I and Q output signals from phase rotator 250 are summed with the corresponding output signals of all the other channels 110 at summing points 262 and 263 to form a first receive beam that produces a stream of 16-bit beam data $S(R,\theta+\Delta\theta_1)$ at an input latch 264. Similarly, the I and Q output signals from phase rotator 252 are summed with corresponding channel output signals at summing points 276 and 268 to form a second receive beam that produces a stream of 16-bit beam sample data $S(R,\theta+\Delta\theta_2)$ at an input latch 269. For a more detailed description of how the I and Q output signals of each receiver channel 110 are summed together to form the two beam signals, see U.S. Pat. No. 4,983,970 which issued on Jan. 8, 1991 and is entitled "Method and Apparatus For Digital Phased Array Imaging", which patent is hereby incorporated by reference. As illustrated in FIG. 8, the receiver thus forms two simultaneous receive beams located about the steering angle $\theta$ by an amount determined by the beam offsets $\Delta\theta_1$ and $\Delta\theta_2$. As will become apparent from the description below, use of these simultaneously-produced receive beams to make the phase measurements required to practice the present invention is an important aspect of the invention.

Referring still to FIG. 6, mid processor 102 (FIG. 3) is structured around a 16-bit processor 280 which drives a 16-bit data bus 281. Processor 280 is programmed to read the receive beam samples from input latches 264 and 269 as they become available, and to load them in the proper location in an $S(R,\theta)$ array 283 in memory 282. As explained in more detail below, when the errors in "beam space" have been adequately sampled, the sample values stored in array 283 are employed to calculate a set of beam space errors ($A\theta$, $\Delta\phi\theta$) stored in memory array 284.

These values are used to define a function $F(\theta)$ which relates measured error to beam angle $\theta$. This function $F(\theta)$ is Fourier transformed to produce 128 "element space" phase correction values $\Delta\phi_k$ which are stored in a memory array 285 and supplied to a latch 286 for application to transmitter 13 (FIG. 1) and receiver beam former 101 (FIG. 3) as described above.

After the phase corrections are provided for a particular beam angle $\theta$, image data subsequently acquired from that angle $\theta$ and the samples $S(R,\theta)$ appear at input latch 264. Processor 280 is programmed to read the I and Q components of these sample values, compute the magnitude values $M(R,\theta)$ as described above, and supply them to shared memory 150 in display system 17 (FIG. 4). A scan is thus comprised of a series of measurements at each beam angle $(\theta)$ which enable phase adjustments to be made to the transmitter and receiver, and then the image data for that beam angle $(\theta)$ are acquired. This is repeated for each of the 128 beam angles $(\theta)$ in the scan.

To perform the scan according to the present invention the program executed by digital controller 16 (FIG. 1) must be adapted to operate in cooperation with the program executed by processor 280 in the receiver (FIG. 6). Before explaining these programs, however, the manner and order in which the phase measurements are made will be described.

Figure 9:
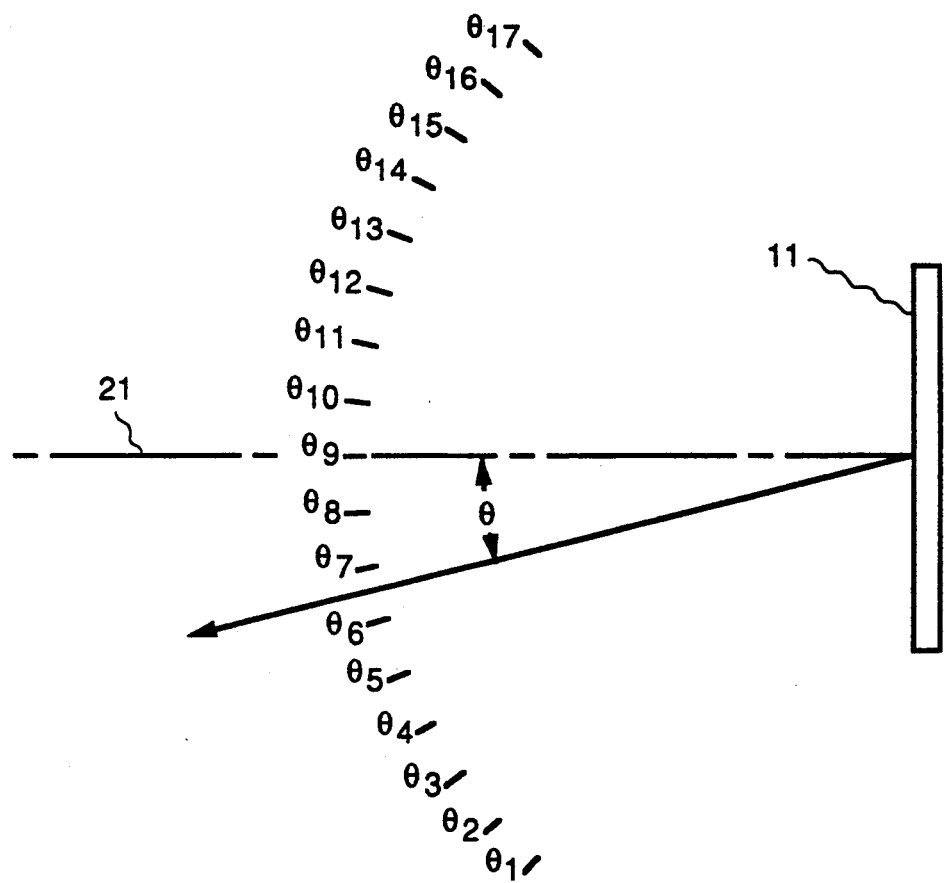
FIG. 9 is a schematic representation of the ultrasonic transducer which illustrates the orientation of the reference beams used to practice the present invention.

Referring particularly to FIG. 9, for each beam angle $\theta$ to be produced during the scan a set of correlation measurements are made by computing the cross-correlation function between the complex, baseband outputs of the two simultaneous receive beams over a finite duration. The signals used for correlation processing emanate from a random, or near-random, collection of scatterers distributed over range. Typically, signals received from the focal zone of the transmitter are used for this purpose. From these correlation measurements the aberration correction phases $\Delta\phi_k$ are produced. In the preferred embodiment of the invention, the correlation measurements are made at seventeen equally spaced reference angles $\theta_1-\theta_{17}$ throughout the 90° sector to be scanned. Two beams are produced simultaneously, one at angle $\theta_0$, and the other at one of the reference angles $\theta_1-\theta_{17}$ as described above, and they are cross correlated over a range segment to calculate both the relative amplitudes $A\theta$ and phases $\Delta\phi\theta$ between the beams. In addition, the autocorrelation of the beam at angle $\theta_0$ is computed for proper normalization.

Figure 10A:
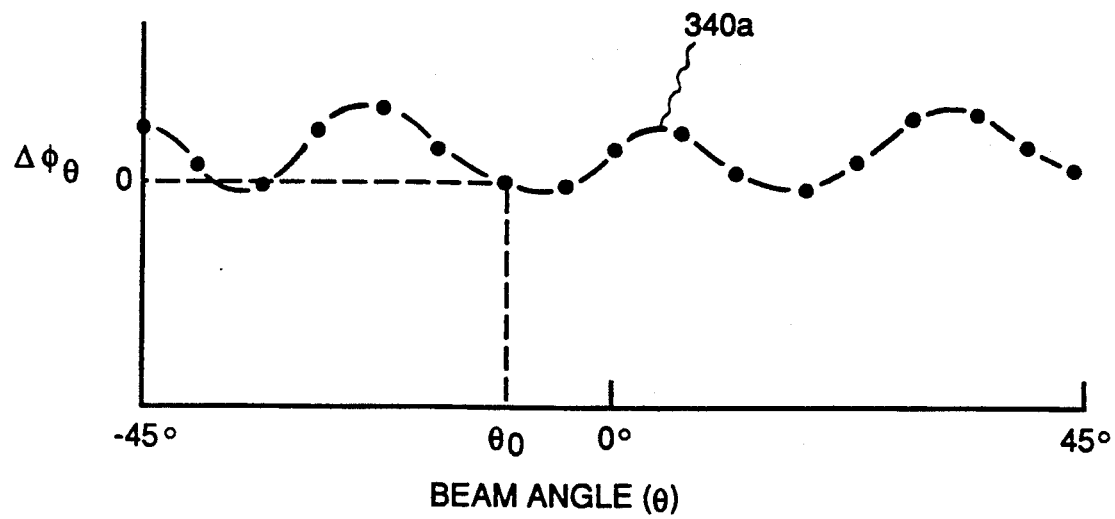
FIGS. 10A and 10B are graphic representations of error measurements made at the reference beam angles according to the present invention.
Figure 10B:
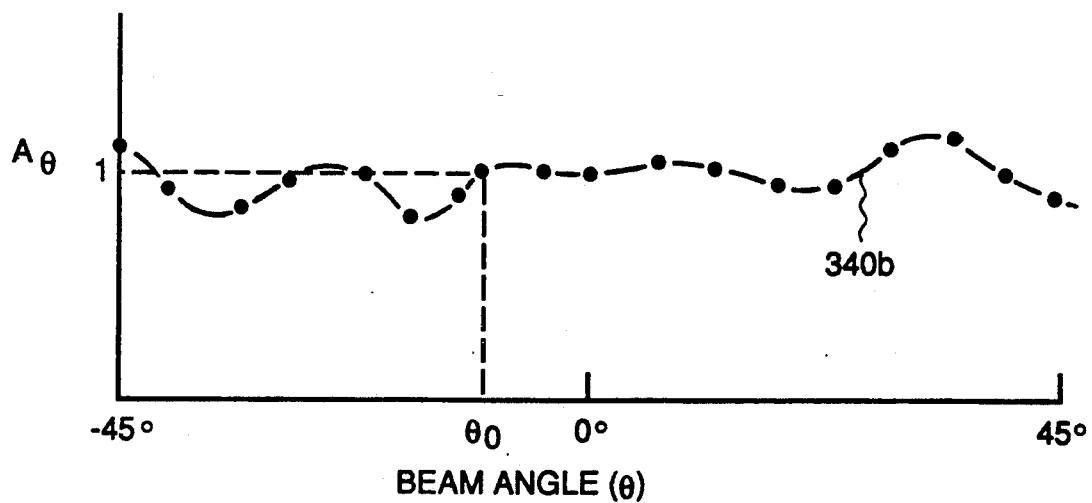

Referring particularly to FIGS. 10a and 10b, after the seventeen correlation measurements are made, a complex function, $F(\theta)$ can be defined by passing a smooth curve through the measured correlation values ($A\theta$, $\Delta\phi\theta$), where the real part of each complex value equals $A\theta \cos \Delta\phi\theta$, and the imaginary part equals $A\theta \sin \Delta\phi\theta$. This function $F(\theta)$ is then sampled at 128 points spaced equally in increments of $\sin\theta$ along the entire range $-45° < \theta < +45°$. These 128 complex samples are fast Fourier transformed to produce 128 phase corrections $\Delta\phi_k$. These 128 phase corrections are applied to the 128 channels in the transmitter and receiver which correspond to the respective 128 transducer elements 12 (FIG. 1). Thus the phase errors are measured in "beam space" and Fourier transformed into "element space" where they can effectively be applied to correct the transmitter and receiver.

Referring again to FIG. 9, while the phase measurements $\Delta\phi\theta$ determine the phase error between the desired beam ($\theta_o$) and each of the seventeen reference angles $\theta_1$ through $\theta_{17}$, in fact, these measurements are obtained indirectly in the preferred embodiment. More specifically, the phase error $\Delta\phi\theta$ is measured between the desired beam ($\theta_0$) and the nearest reference angle ($\theta_7$ in FIG. 9), and the phase error $\Delta\phi\theta$ is then measured between adjacent pairs of reference angles ($\theta_7 - \theta_8$, $-\theta_9$, $\theta_9 - \theta_{10}$, etc.). The phase error $\Delta\phi\theta$ between the desired beam angle ($\theta_0$) and each of the reference angles $\theta_1$ through $\theta_{17}$ is then calculated by adding together the separate, "incremental" measurements. In this manner the phase errors throughout the 90° sector can be measured using two simultaneous receive beams that are separated from one another by less than six degrees.

Figure 11:
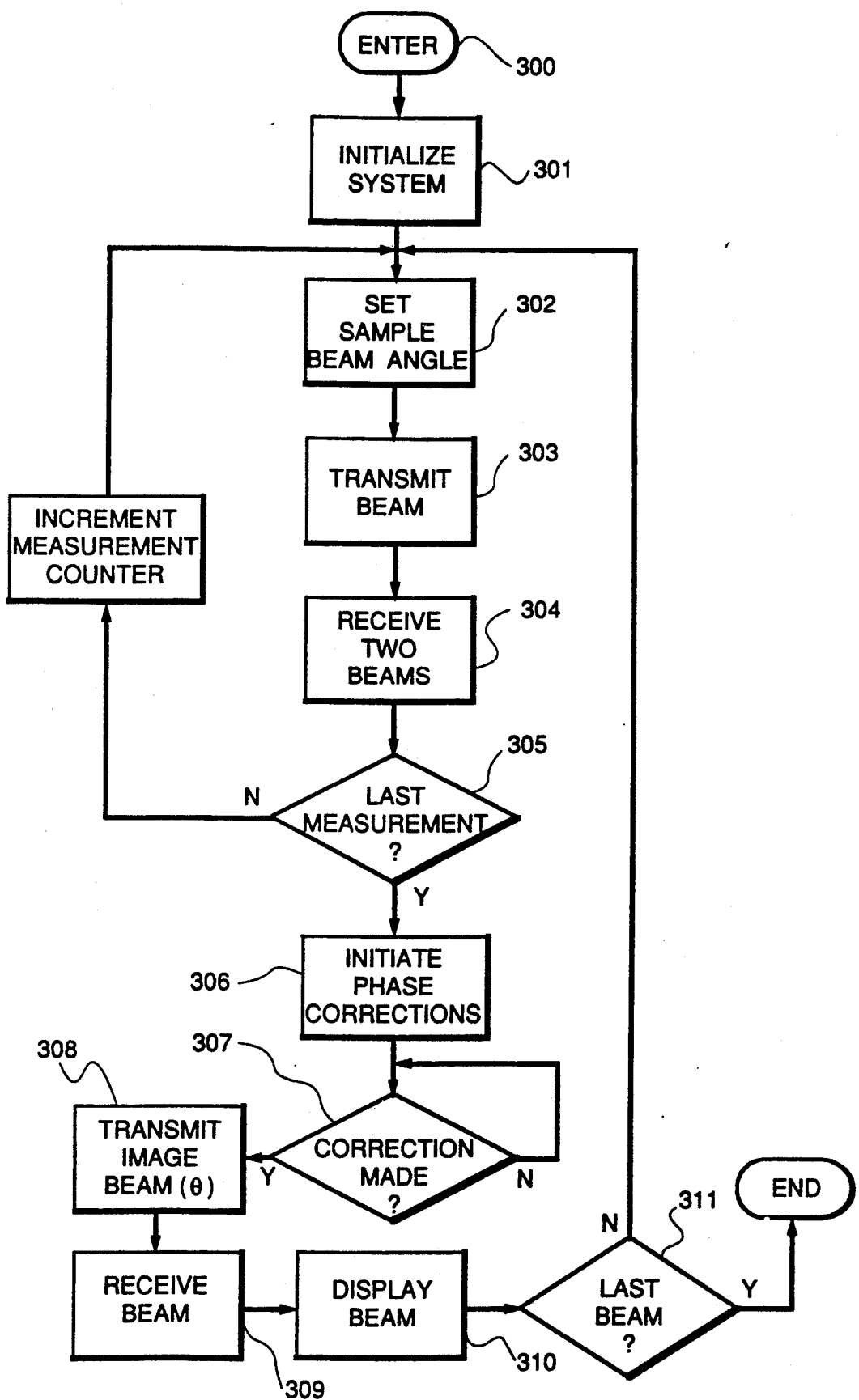
FIG. 11 is a flow chart of the scan program executed by the digital controller of FIG. 1.

Referring particularly to FIG. 11 in conjunction with FIG. 1, to carry out the preferred embodiment of the present invention, digital controller 16 executes a scan program entered at step 300. Data structures including a phase correction flag and a reference angle counter are initialized at process step 301, and then a loop is entered in which the phase measurements for a desired beam angle $(\theta)$ are made. As indicated at process step 302, the sample angle of each phase measurement is calculated such that the transmit beam is directed toward the reference angle closest to the desired beam angle $(\theta)$, and the two receive beams are directed at two of the reference beam directions. Referring to FIG. 9, for example, if the phase error between reference angles $\theta_7$ and $\theta_8$ is to be measured, the transmit beam is directed at the closest reference angle ($\theta_0 = \theta_7$) and the receive beams are directed at the angles $\theta_7$ and $\theta_8$. The beam is transmitted, as indicated at process step 303, and two receive beams are received at process step 304. The phase shift commands $\Delta\theta_1$ and $\Delta\theta_2$ provided to the receiver during the reception of the echo signal are set to direct the two receive beams at the pair of reference angles $\theta_1-\theta_{17}$ being measured, and the timing of the receive beam former is set to a beam directed midway between these two reference angles. This process continues as described above until all seventeen of the correlation measurements have been made as determined at decision step 305.

After correlation data have been acquired, a phase correction message is supplied to the mid processor of receiver 14 to indicate that the phase corrections should be calculated as indicated at process step 306. Digital controller 16 then waits at decision step 307 for a return message which indicates that the calculations have been made and the aberration correction phases $\Delta\phi_k$ have been applied to transmitter 13 and receiver 14 as described above. Then, transmitter 13 is enabled at process step 308 of FIG. 11 to generate an ultrasonic pulse steered at the beam angle ($\theta$) and receiver 14 is enabled at process step 309 to receive the resulting echo signal. The series of received beam samples are provided to display system 17 at process step 310 to produce one line, or beam, of data on the display screen. The scan program loops back to produce another beam in the image until all 128 beams have been produced as determined at decision step 311.

It should be apparent to those skilled in the art that a number of variations are possible in the manner in which the scan is performed. For example, it is not always necessary to remeasure the incremental phase differences for each beam angle ($\theta$). Instead, independent measurements can be made at each of the reference angles to characterize the phase errors $\Delta\phi_k$ as a function of steering beam angle $\theta$. For beam angles between these reference angles, interpolation may be employed using the phase errors $\Delta\phi_k$ from the two adjacent reference angles. Also, measurements need not be made on every frame. A measurement may be applied to several frames of data before a new measurement is made. The rate at which the full set of phase measurements are made may be operator selectable so that the physician can trade off image quality and total scan time as the examination is being performed.

Figure 12:
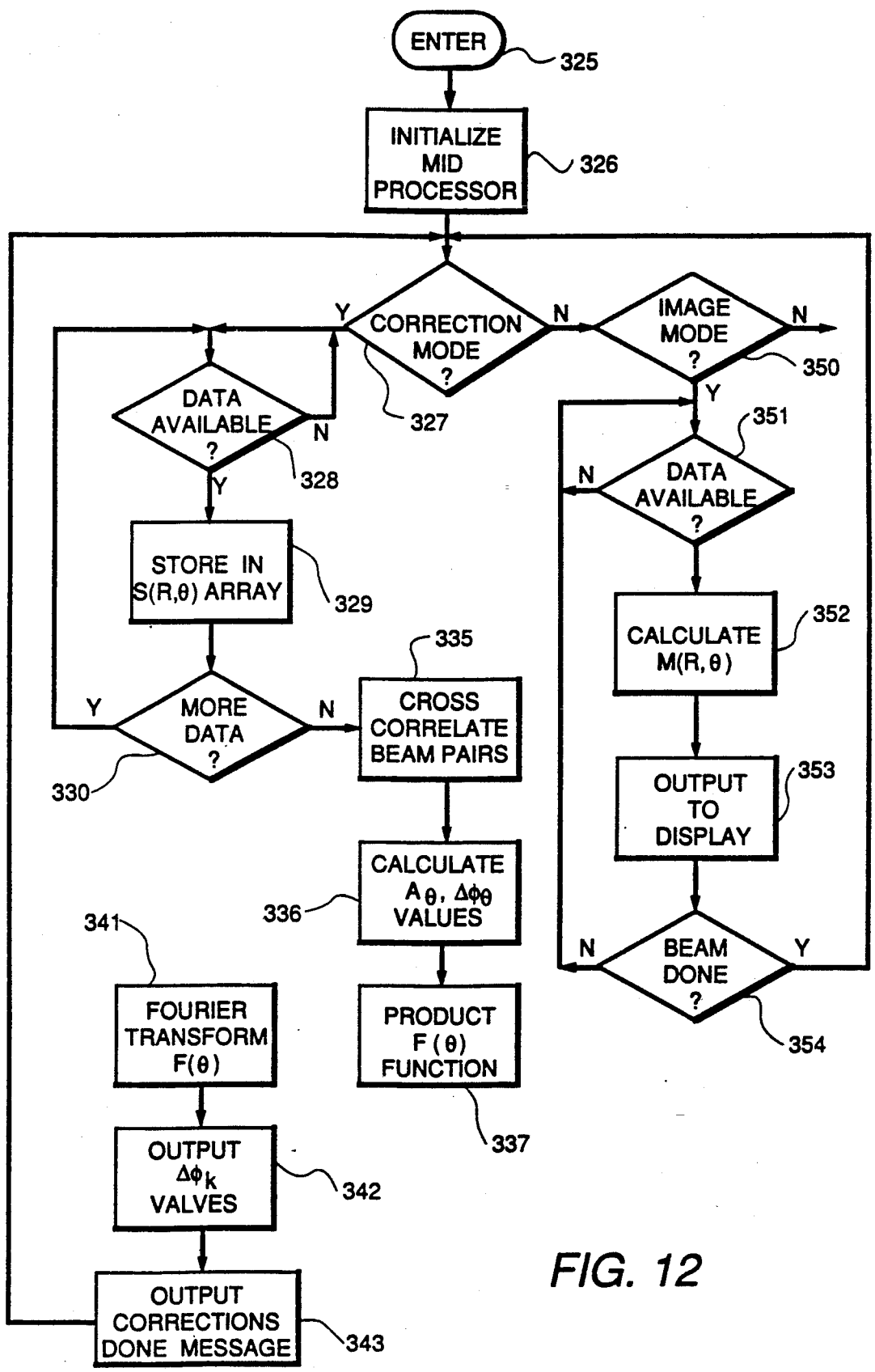
FIG. 12 is a flow chart of the program executed by the mid-processor of FIG. 6 to carry out the present invention.

Referring particularly to FIG. 12, processor 280 (FIG. 6) in mid processor 102 (FIG. 3) is programmed to receive the sample beam data and either use it to calculate aberration phase corrections $\Delta\phi_k$ or produce a beam of image data for display system 17 (FIG. 1). The program is entered at step 325 and data structures such as a "corrections done" flag are initialized at process step 326 before determining what mode the mid processor is in. If the mid processor is in the aberration correction mode as determined at decision step 327, it waits in accordance with decision step 328 until receive data are available. As indicated above, the mid processor is placed in this mode by a message from digital controller 16 (FIG. 1).

Referring particularly to FIGS. 6 and 12, when data are available at input latches 264 and 269, as determined at decision step 328, the data are read and stored in $S(R,\theta)$ array 283 as indicated at process step 329. When seventeen pairs of beam data have been acquired, a message is received from digital controller 16 indicating that phase corrections are to be calculated. This is detected at decision step 330, and at this time $S(R,\theta)$ array 283 stores the data illustrated in FIG. 13.

Figure 13:
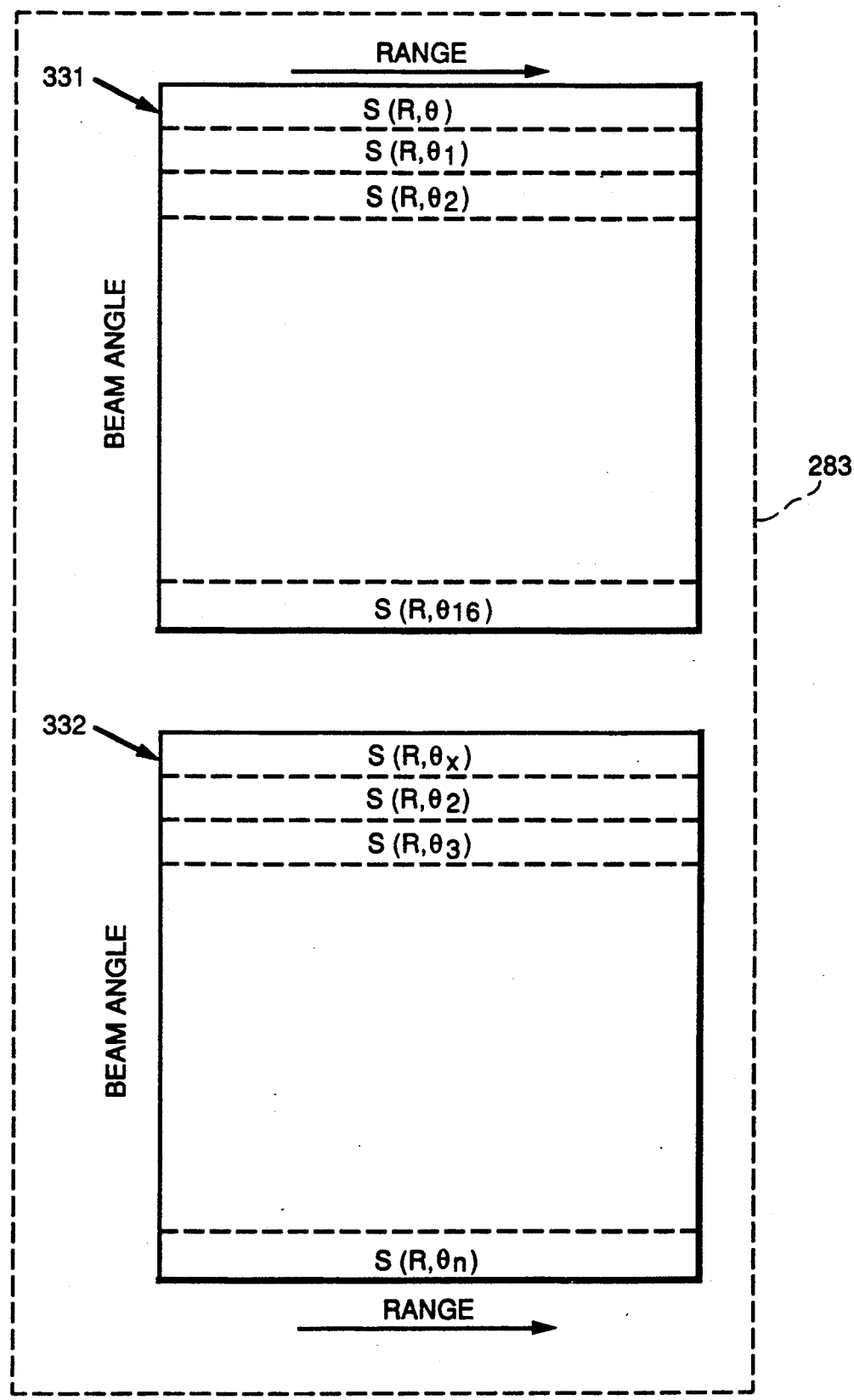
FIG. 13 is a schematic representation of data structure in the mid-processor of FIG. 6 produced while practicing the present invention.

Array 283 of FIG. 6 is comprised of two two-dimensional arrays 331 and 332, shown in FIG. 13. Each row of array 331 stores the beam samples from input latch 264 (FIG. 6) and the corresponding row in array 332 stores the beam samples from the simultaneously received beam. The first row of beam sample data in array 331 measures the echo signal along the desired beam angle ($\theta$) and the corresponding first row in array 332 stores the simultaneously acquired data from the nearest reference angle $\theta_x$. Subsequent rows in arrays 331 and 332 represent the simultaneously-acquired pairs of adjacent reference beam data.

Referring again to FIG. 12, after the correlation measurement data have been acquired the first step is to calculate the cross-correlation of the echo signal pairs over a set of ranges as indicated at process step 335. This is accomplished by cross correlating corresponding rows in arrays 331 and 332 (FIG. 13) with each other. This produces a set of seventeen correlation amplitude and phase difference values. In the preferred embodiment, each cross correlation is performed by multiplying a complex sample in one beam by the complex conjugate of the corresponding complex sample in the other beam at a set of ranges in the center of the image, and averaging the results. Then, as indicated at process step 336, these incremental differences are added together as described above to provide the complex errors $A_{1-17}$ and $\Delta\phi_{1-17}$ which indicate the error in the desired beam patterns. FIG. 10A shows the phase shift values $\Delta\phi_\theta$ as a function of beam angle ($\theta$) while, in FIG. 10B, the relative amplitude values $A_\theta$ are normalized to the amplitude of the autocorrelation of the reference beam $\theta_0$ amplitude (i.e. $\theta_7$ in the above example) and are also shown as a function of beam angle ($\theta$).

Next, as indicated at process step 337 of FIG. 12, a smooth curve is passed through the above-mentioned seventeen relative amplitude and phase error measurements to produce a complex error function $F(\theta)$, which measures the complex error (i.e. magnitude and phase) as a function of beam angle, as shown by the dashed lines 340a and 340b in FIGS. 10A and 10B. This error function $F(\theta)$ is sampled at 128 points and these samples, as indicated at process step 341 of FIG. 12, undergo a fast Fourier transformation. This produces 128 phase correction values $\Delta\phi_k$ for each transmit beam angle $\theta$. These are provided, at process step 342, to transmitter 13 (FIG. 1) and receiver channels 110 (FIG. 3) as described above. A "corrections done" message is then sent to digital controller 16 (FIG. 1) at process step 343, and the mid processor loops back to determine its next mode of operation. Again, an independent set of correction values $\Delta\phi_k$ need not be acquired for every transmit beam angle $\theta$ used in the scan. A reduced set of correction values $\Delta\phi_k$ can be acquired for transmit beams directed along the reference angles. Interpolation can then be used to produce accurate estimates of the correction values $\Delta\phi_k$ at transmit beam angles $\theta$ between these reference angles.

Referring still to FIG. 12, after the phase corrections have been made by the mid processor, the mid processor is placed in the image mode, which is detected at decision step 350. The mid processor waits until beam samples are available at input latch 264 (FIG. 6), and when they are available, as determined at decision step 351, the detection processor operates to calculate the corresponding magnitude $M(R,\theta)$, as indicated at process step 352. This magnitude value is supplied to display system 17 (FIG. 1) at process step 353 and a test is then made at decision step 354 to determine if the entire beam at angle ($\theta$) has been acquired. If so, the mid processor loops back to determine its next mode of operation; if not, the mid processor loops back to await more beam samples before again undergoing decision step 351.

While only certain preferred features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A coherent vibratory energy beam imaging system which corrects for aberrations in transmission media for said beam, comprising:
- a transducer array having a set of array elements disposed in a pattern and each being separately operable to produce a pulse of vibratory energy during a transmission mode and to produce an echo signal in response to vibratory energy impinging thereon during a receive mode;
- a transmitter coupled to said transducer array and being operable during the transmission mode to apply a separate signal pulse to each array element such that a steered transmit beam is produced;
- a receiver coupled to said transducer array and being operable during the receive mode to sample the echo signal produced by each array element as the vibratory energy impinges thereon and to form a plurality of simultaneous receive beam signals therefrom by summing the separate echo signals sampled from each array element;
- controller means coupled to said transmitter and said receiver and being operable to perform a scan during which a set of correlation measurements is made periodically to measure phase of the echo signals steered in a set of reference beam angles with respect to the echo signal steered in a desired beam angle ($\theta$); and
- processor means coupled to said transmitter, said receiver and said controller means and being operable in response to the simultaneous receive signals produced as a result of the periodic correlation measurements to generate a set of errors (A$\theta$, $\Delta\phi_\theta$) and perform a Fourier transformation thereon to produce a set of aberration phase corrections $\Delta\phi_k$ for application to the transmitter and the receiver to correct the phase of the signals applied to and produced by said each array element in the transducer array.

2. The coherent vibratory energy beam imaging system recited in claim 1 wherein said controller means comprises means for cross correlating a portion of the simultaneous receive beam signals.

3. The coherent vibratory energy beam imaging system recited in claim 1 wherein said receiver includes means for producing a pair of simultaneous receive beam signals from the echo signals 4. The coherent vibratory energy beam imaging system recited in claim 1 wherein said processor means includes interpolation means for generating aberration phase corrections for any beam angle.

5. In an ultrasonic imaging system, a method of correcting for aberrations in transmission media for said beam, comprising:
- energizing a set of ultrasonic transducer array elements in an ultrasonic transducer array, said array elements being disposed in a pattern and each being separately operable in response to a separate signal pulse applied to each array element during a transmission mode such that a steered transmit beam is produced, said array elements further being separately operable to produce an echo signal in response to ultrasonic energy impinging thereon during a receive mode;
- sampling the echo signal produced by each array element as the ultrasonic energy impinges thereon;
- forming a plurality of simultaneous receive beam signals from said set of array elements by summing the separate echo signals sampled from each array element;
- performing a scan in which a set of correlation measurements is made periodically during the scan to measure phase of the echo signals steered in a set of reference beam angles with respect to the echo signal steered in a desired beam angle ($\theta$);
- generating a set of errors (A$\theta$, $\Delta\phi_\theta$) in response to the simultaneous receive signals produced as a result of the periodic correlation measurements; and
- Fourier transforming the set of errors (A$\theta$, $\Delta\phi_\theta$) to produce a set of aberration phase corrections $\Delta\phi_k$ for correcting the phase of the signals applied to and produced by each array element in the ultrasonic transducer array.

6. The method recited in claim 5 wherein the set of correlation measurements is made prior to acquiring each beam of sample data employed to reconstruct an image and the aberration phase corrections $\Delta\phi_k$ are coupled to the transmitter and receiver prior to the acquisition of each such beam of sample data.

7. The method recited in claim 5 wherein each correlation measurement is made by cross correlating a portion of the simultaneous receive beam signals.

8. The method recited in claim 5 wherein a pair of simultaneous receive beam signals is generated from the echo signals, and wherein each correlation measurement is made by cross correlating a portion of the beam sample data from said pair of simultaneous receive beam signals.

9. The method of claim 8 wherein one of said correlation measurement in each set thereof includes receive beam signals steered in the desired beam angle ($\theta$) and receive beam signals steered in one of said reference beam angles, and wherein the remaining correlation measurements in said each set thereof includes receive beam signals steered in two of said reference beam angles.

10. The method recited in claim 5 wherein each correlation measurement is made from a set of receive beam signals emanating from a random collection of sound scatters.

11. The method recited in claim 9 wherein the beam angle ($\theta$) transmitted for aberration correction processing corresponds in direction to one of said reference beam angles.

* * * * *